United States Patent [19]

Merkl

[11] 4,052,429
[45] * Oct. 4, 1977

[54] METHOD OF FORMING A COMPOUND CONTAINING ALUMINUM AND GLYCEROL

[76] Inventor: George C. Merkl, 46 Sunset Court, Haworth, N.J. 07641

[*] Notice: The portion of the term of this patent subsequent to Dec. 24, 1991, has been disclaimed.

[21] Appl. No.: 540,786

[22] Filed: Jan. 13, 1975

[51] Int. Cl.$^2$ ............................................... C07F 5/06
[52] U.S. Cl. ........................... 260/448 AD; 260/2 M; 424/78; 424/80; 424/81
[58] Field of Search ...................... 260/448 AD, 2 M; 424/78, 80, 81

[56] References Cited
U.S. PATENT DOCUMENTS

| | | | |
|---|---|---|---|
| 1,793,935 | 2/1931 | Kaufler et al. | 260/448 AD |
| 2,125,961 | 8/1938 | Shoemaker et al. | 260/448 AD |
| 2,292,205 | 8/1942 | Denison et al. | 260/448 AD |
| 2,440,750 | 5/1948 | Kraus et al. | 260/448 AD |
| 2,796,326 | 6/1957 | Kimberlin et al. | 260/448 AD |
| 3,198,332 | 8/1965 | Davison | 260/448 AD |
| 3,305,571 | 2/1967 | Cenker | 260/448 AD |
| 3,352,895 | 11/1967 | Holbert et al. | 260/448 AD |
| 3,671,545 | 6/1972 | Halpern | 424/80 X |
| 3,751,565 | 8/1973 | Santorelli | 424/80 |
| 3,856,841 | 12/1974 | Merkl | 260/448 AD X |

OTHER PUBLICATIONS
Chemical Abstracts, 51, 12724a (1957).

*Primary Examiner*—Helen M. S. Sneed
*Attorney, Agent, or Firm*—Arnold, White & Durkee

[57] ABSTRACT

Compounds containing aluminum and glycerol are prepared by a method which comprises
contacting and reacting:
 a. a reactive aluminum comprising aluminum of a purity of at least 99.9% by weight, permeated with a liquid metal selected from mercury, gallium and indium/gallium alloys;
in a reaction medium comprising
 b. glycerine; and
 c. a liquid selected from
  i. water;
  ii. lower alcohols;
  iii. glycols; and
  iv. phenols.

The reactive aluminum is consumed during the reaction forming the compound containing aluminum and glycerol. The reaction is terminated to recover the desired compound by withdrawing any unreacted reactive aluminum from the reaction medium.

The products of this reaction can be utilized as water soluble resins or plasticizers for resin systems.

9 Claims, No Drawings

METHOD OF FORMING A COMPOUND CONTAINING ALUMINUM AND GLYCEROL

RELATED CO-PENDING PATENT APPLICATIONS

Reference is had to applicant's co-pending patent application, Ser. No. 497,560, filed Aug. 15, 1974, entitled "Reactive Metals".

BACKGROUND OF THE INVENTION

This invention relates to a method of forming compounds containing aluminum and glycerol and such compounds so produced. The compounds of the method of the present invention find utility as water soluble resins and plasticizers for resin systems.

SUMMARY OF THE INVENTION

Compounds containing aluminum and glycerol, useful as water soluble resins or plasticizers for resin systems, are prepared in accordance with the present invention by a method which comprises:

contacting and reacting:
a. a reactive aluminum comprising aluminum of a purity of at least about 99.9% by weight, permeated with a liquid metal selected from mercury, gallium and indium/gallium alloys;
in a reaction medium comprising:
b. glycerol; and
c. a liquid selected from water, lower alcohols, glycols, and phenols.

Such contact and reaction results in consumption of the reactive aluminum, forming the aluminum and glycerol containing compound. The reaction is terminated to recover such aluminum and glycerol containing compound by withdrawing any unreacted reactive aluminum from the reaction medium. Generally, the reaction is terminated when the desired compound contains from about 1 to about 10% by weight aluminum, preferably from about 1 to about 3% by weight aluminum.

The reaction in accordance with the present invention can be accelerated by adding to the reaction medium up to 5% by weight an organic or inorganic acid. The products produced by this reaction are useful as water soluble resins or plasticizers for resins systems. A medicament can be added to this reaction product either during or subsequent to the reaction.

DESCRIPTION OF THE PREFERRED EMBODIMENTS

In carrying the invention into effect, several embodiments have been selected for description in the specification.

The instant invention utilizes a reactive aluminum described in the aforementioned co-pending application. In order to avoid an extensive repetition of the teachings of that co-pending application, the disclosure of that co-pending application is incorporated herein by reference and a brief summary of that disclosure is presented herein.

Generally, a reactive aluminum for the instant invention is prepared by permeating aluminum having a purity of at least about 99.9 per cent with at least one metal selected from the group consisting of gallium, indium, and mercury.

In accordance with the present invention, it is preferred that the metal permeating the aluminum is a liquid metal. Accordingly, preferred metals are mercury, gallium, and indium/gallium alloys.

The reactive aluminum is prepared by contacting the aluminum and the selected metal in the presence of a hydrogen ion source selected from the group consisting of aqueous acids, aqueous alkaline solutions, and alcohols. Due to the hydrogen ions available, it is presumed in accordance with the present invention that the metal permeating the aluminum permeates in the form of a hydride.

Preferably, the second metal should have a purity of at least about 99.9 per cent by weight.

In a case of the use of mercury, at least about 0.1 per cent preferably at least 1 per cent by weight is permeated in the aluminum. The aluminum inherently sets the upper limit at about 5 per cent by weight as additional mercury is not retained therein.

For gallium or indium, only about 0.01 per cent by weight is needed and about 0.1 per cent by weight is preferable. Again, the maximum of about 3 per cent is determined by the ability of the aluminum to retain the gallium or indium.

Preferably, the temperature of the aluminum during the permeation should not exceed 200° F and should be about 70° F.

The acid for the permeation can be an inorganic acid, such as hydrochloric acid or hydrobromic acid or the like or an organic acid, such as citric acid or acetic acid or the like. The alkaline solution can be an aqueous solution of sodium hydroxide, potassium hydroxide, or the like.

In the case where the aluminum and the selected metal are contacted in the presence of an aqueous acid or an aqueous alkaline solution or an alcohol, it is preferable to have the aluminum completely covered by the liquid to avoid the formation of a product described in the applicant's co-pending application, Ser. No. 176,907, filed Sept. 1, 1971 now abandoned.

Typically, an aluminum rod 4-inches long and ½ inch in diameter can be formed into a reactive aluminum in less than a half-hour and in some cases less than 5-minutes, depending upon the temperature of the reactants and the activity of the hydrogen ion source. It may be desirable to remove the oxide coating on the aluminum mechanically or to use a strong acid prior to the permeation by the selected metal hydride.

Generally, a composition including aluminum and glycerol, suitable for use as a water soluble resin and/or a plasticizer is formed by reacting the reactive aluminum with glycerol and at least one liquid selected from the group consisting of water, lower alcohols, glycols and phenols. Of course, other liquid organic compounds can be used.

Water and lower alcohols, particularly non-toxic alcohols such as ethanol, are of particular interest in view of their immediate use in industries such as the food and detergent industries where the toxic nature of chemicals are of considerable concern. Surprisingly, the instant composition can contain from about 10 to about 60 per cent by weight water and/or alcohol. The use of water alone yields an aluminum glycerohydrate.

The amount of aluminum appearing in the composition generally varies from about 1 to about 10 per cent by weight and appears to depend upon the amount of alcohol forming part of the composition.

Methanol, isopropyl alcohol, butanol and the like can be used in the invention.

Glycols, such as ethylene glycol, diethylene glycol, triethylene glycol, and the like can be used in the instant invention.

The phenols includes hydroxybenzene, usually called phenol, cresols, naphthols and the like.

In carrying out the instant invention, it may be desirable to add an organic or inorganic acid or the like in order to accelerate the formation of the composition. Less than about 5 per cent by weight of such an acid can be used.

In the case where the composition, according to the invention is to be used to form a thin film, it has been found that an aluminum content by weight of greater than about 3 per cent tends to make the film brittle. An aluminum content of about 2 per cent has been found preferable, but of course, the proportion of the glycerol by weight and the selected liquid are further factors determining the quality and properties of the composition.

Surprisingly, the composition according to the instant invention can be added to a known water soluble resin to obtain a considerably improved resin. In particular, the known water soluble resins include methyl and hydroxypropyl methyl-cellulose derivatives, hydroxethylcellulose, carboxymethylcellulose, polyvinyl alcohol, polyvinylpyrrolidone, polyacrylic acid and its homologs, polyacrylamide, ethylene oxide polymers and polyethylenimine.

Generally, from about 0.5 to about 5 per cent by weight, preferably 2 per cent by weight, of the composition according to the instant invention is added to a known water soluble resin to obtain improved physical properties, such as strength and flexibility without carrying in the problem of being hygroscopic.

The composition of the instant invention can be used to carry a medicament for use in the medical treatment of cuts and the like. For example, the composition can be sprayed onto a wound and thereby form a water soluble film over a wound while carrying medicine into the wound. Iodine can be used in the formation of the composition to accelerate the reaction. The iodine serves as an antiseptic in a subsequent use of the composition in the medical field. The active medical constituent can be added to the composition after it has been formed. Of course, the instant composition prepared with an alcohol, particularly in a large proportion by weight, will inherently have good germ killing power.

Illustrative, non-limiting examples of the practice of the invention are set out below. Numerous other examples can readily be evolved in the light of the guiding principals and teachings herein. The examples are intended to illustrate the invention and not in any sense to limit the manner in which the invention can be practiced. The parts and percentages recited herein and all through the specification and claims, unless specifically provided otherwise, refer to parts by weight and percentages by weight.

EXAMPLE 1

A resin according to the present invention is formed by reacting about 1000 grams of glycerol, about 500 grams of ethanol, and about 108 grams of a reactive aluminum. The reaction is operated as a reflux at about 160° F for about 12 hours.

EXAMPLE 2

Example 1 is repeated but, instead of ethanol, methanol or isopropyl alcohol or butanol or isobutanol or phenol or ethylene glycol is used.

EXAMPLE 3

Examples 1 and 2 are repeated except that from about 50 to about 100 grams of hydrochloric acid or hydrobromic acid or iodine are added to the reaction.

EXAMPLE 4

An aluminum glycerohydrate according to the present invention is formed by reacting about 1000 grams of glycerol, about 500 grams of water, and about 108 grams of a reactive aluminum. In addition, about 500 grams of ethanol can be added.

EXAMPLE 5

Repeat Example 4 but use about 1000 grams of water and react about 12 hours for a good quality film forming water soluble resin.

EXAMPLE 6

A product suitable for the medical treatment of a wound is formed by the following: react about 450 grams of glycerol, about 450 grams of ethanol, about 126 grams of iodine, and about 150 grams of a reactive aluminum about 24 hours to form a water soluble film forming resin and add about 1 gram of this resin to about 5 grams of carboxymethylcellulose, and about 50 grams of ethanol to form a "first aid" product which can be sprayed onto a wound. If the iodine is omitted from the first reaction, other effective medicaments can be substituted and optimized experimentally or a medicament can be added in the second step where no reaction with the reactive aluminum occurs.

EXAMPLE 7

A resin exhibiting good industrial properties is formed by reacting about 2 grams of any of the products of examples 1 to 5 to about 45 grams of water and about 100 grams of carboxymethylcellulose or methylcellulose and heating to about 130° F for about 30 minutes.

I claim:

1. A method of forming a compound containing aluminum and glycerol which comprises:
    contacting and reacting:
    a. a reactive aluminum comprising aluminum of a purity of at least about 99.9% by weight permeated with a liquid metal selected from mercury, gallium and indium/gallium alloys;
    in a reaction medium consisting essentially of:
    b. glycerol; and
    c. a liquid selected from
        i. water;
        ii. lower alcohols;
        iii. glycols; and
        iv. phenols,
    said reactive aluminum being consumed during the reaction to form said compound containing aluminum and glycerol; and
    terminating the reaction to recover said compound containing aluminum and glycerol by withdrawing any unreacted reactive aluminum from the reaction medium.

2. The method of claim 1 wherein the reaction is terminated when said compound containing aluminum and glycerol contains from about 1 to about 10% by weight aluminum.

3. The method of claim 2 wherein the reaction is terminated when said compound containing aluminum and glycerol contains from about 1 to about 3% by weight aluminum.

4. The method of claim 1 wherein said liquid (c) is water.

5. The method of claim 1 wherein said liquid (c) is a lower alcohol.

6. The method of claim 1 wherein said liquid (c) is a glycol.

7. The method of claim 1 wherein said liquid (c) is a phenol.

8. The method of claim 1 further including adding to the reaction medium up to 5% by weight of an organic or inorganic acid to accelerate the reaction.

9. The method of claim 1 wherein said reactive aluminum comprises aluminum metal of a purity of at least about 99.9% by weight permeated with from about 0.1% to about 5.0% by weight mercury.

* * * * *